(12) United States Patent
Supattapone et al.

(10) Patent No.: US 7,871,776 B2
(45) Date of Patent: *Jan. 18, 2011

(54) COMPOSITIONS AND METHODS FOR ENHANCING THE IDENTIFICATION OF PRIOR PROTEIN PRP$^{Sc}$

(75) Inventors: Surachai Supattapone, Hanover, NH (US); Nathan Deleault, Canaan, NH (US)

(73) Assignee: Trustees of Dartmouth College, Hanover, NH (US)

( * ) Notice: Subject to any disclaimer, the term of this patent is extended or adjusted under 35 U.S.C. 154(b) by 35 days.

This patent is subject to a terminal disclaimer.

(21) Appl. No.: 12/090,101

(22) PCT Filed: Jan. 8, 2007

(86) PCT No.: PCT/US2007/060201

§ 371 (c)(1),
(2), (4) Date: Apr. 14, 2008

(87) PCT Pub. No.: WO2007/082173

PCT Pub. Date: Jul. 19, 2007

(65) Prior Publication Data

US 2008/0261316 A1    Oct. 23, 2008

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

| | | | | |
|---|---|---|---|---|
| 6,239,157 | B1 * | 5/2001 | Mbalaviele | 514/369 |
| 6,406,907 | B1 * | 6/2002 | Taylor et al. | 435/325 |
| 6,670,328 | B1 * | 12/2003 | Lassalle et al. | 514/12 |
| 7,407,760 | B2 * | 8/2008 | Supattapone et al. | 435/6 |
| 2002/0001817 | A1 * | 1/2002 | Prusiner et al. | 435/7.1 |
| 2002/0137114 | A1 | 9/2002 | Voelkel et al. | 435/7.92 |

OTHER PUBLICATIONS

Saborio et al. (Biochem Biophys Res Commun. May 10, 1999;258(2):470-5).*
Stratagene ("Gene Characterization Kits" 1988).*
Ahmad et al. (Thromb Res. Jul. 1, 1989;55(1):121-33).*
Bessen et al., "Non-genetic propagation of strain-specific properties of scrapie prior protein", Nature 1995 375:698-700.
Brimacombe et al., "Characterization and polyanion-binding properties of purified recombinant prior protein", Biochem. J. 1999 342:605-613.
Brown et al., "Consequences of manganese replacement of copper for prion protein function and proteinase resistance", The EMBO Journal 2000 19(6):1180-1186.
Caughey, B., "Formation of Protease-Resistant Prion Protein in Cell-Free Systems", Curr. Issues Mol. Biol. 2000 2(3):95-101.
Cordeiro et al., "DNA Converts Cellular Prion Protein into the β-Sheet Conformation and Inhibits Prion Peptide Aggregation", J. Biol. Chem. 2001 276(52):49400-49409.
Derrington et al., "PrP$^c$ has nucleic acid chaperoning properties similar to the nucleocapsid protein of HIV-1", C.R. Biologies 2002 325:17-23.
Gabus et al., "The Prion Protein Has RNA Binding and Chaperoning Properties Characteristic of Nucleocapsid Protein NCp7 of HIV-1", J. Biol. Chem. 2001 276(22):19301-19309.
Gabus et al., "The Prion Protein has DNA Strand Transfer Properties Similar to Retroviral Nucleocapsid Protein", J. Mol. Biol. 2001 307:1011-1021.
Horiuchi et al., "Specific binding of normal prion protein to the scrapie form via a localized domain initiates its conversion to the protease-resistant state" The EMBO Journal 1999 18(12):3193-3203.
Horiuchi et al., "Prion protein interconversions and the transmissible spongiform encephalopathies", Structure 1999 7(10):R231-R240.
Kocisko et al., "Species specificity in the cell-free conversion of prion protein to protease-resistant forms:A model for the scrapie species barrier", Proc. Natl. Acad. Sci. USA 1995 92:3923-3927.
Kocisko et al., "Cell-free formation of protease-resistant prion protein", Nature 1994 370:471-474.
Moscardini et al., "Functional Interactions of Nucleocapsid Protein of Feline Immunodeficiency Virus and Cellular Prion Protein with the Viral RNA", J. Mol. Biol. 2002 318:149-159.
Nandi et al., "DNA-induced Partial Unfolding of Prion Protein Leads to its Polymerisation to Amyloid", J. Mol. Biol. 2002 322:153-161.
Nandi et al., "Unusual Property of Prion Protein Unfolding in Neutral Salt Solution", Biochemistry 2002 41:11017-11024.
Proske et al., "Prion-Protein-Specific Aptamer Reduces PrP$^{Sc}$ Formation", ChemBioChem 2002 3:717-725.

(Continued)

*Primary Examiner*—Christopher M. Babic
(74) *Attorney, Agent, or Firm*—Licata & Tyrrell P.C.

(57) ABSTRACT

A method for purifying PrP$^c$, a purified preparation of PrP$^c$ and methods and kits for identifying the presence of PrP$^c$ are provided.

1 Claim, No Drawings

OTHER PUBLICATIONS

Saborío et al., "Cell-Lysate Conversion of Prion Protein into Its Protease-Resistant Isoform Suggests the Participation of a Cellular Chaperone", Biochemical and Biophysical Research Communications 1999 258:470-475.

Warner et al., "Identification of the Heparan Sulfate Binding Sites in the Cellular Prion Protein", J. Biol. Chem. 2002 277(21):18421-18430.

Weiss et al., "RNA Aptamers Specifically Interact with the Prion Protein PrP", Journal of Virology 1997 71(11):8790-8797.

Zeiler et al., "Concentration and removal of prion proteins from biological solutions", Biotechnol. Appl. Biochem. 2003 37:137-182.

Pan et al., "Conversion of $\alpha$-helices into $\beta$-sheets featuresin the formation of the scrapie prion proteins", Proc. Natl. Acad. Sci. USA 1993 90:10962-10966.

Saborio et al. ("Sensitive detection of pathological prion protein by cyclic amplification of protein misfolding" Nature. Jun. 14, 2001;411(6839):810-3).

Saborio at al. ("Cell-lysate conversion of prion protein into its protease-resistant isoform suggests the participation of a cellular chaperone" Biochem Biophys Res Commun. May 10, 1999;258(2):470-5).

* cited by examiner

COMPOSITIONS AND METHODS FOR ENHANCING THE IDENTIFICATION OF PRIOR PROTEIN PrP$^{Sc}$

This invention was made in the course of research sponsored by the National Institutes of Health (NIH Grant Nos. K08 NS02048-04, AI058979, and NS046478). The U.S. government has certain rights in this invention.

This application is a National Phase of PCT/US2007/060201 filed Jan. 8, 2007 which claims priority to U.S. Ser. No. 11/327,993 filed Jan. 9, 2006, issued as U.S. Pat. No. 7,407,760, each of which are herein incorporated by reference in their entireties.

This invention was made in the course of research sponsored by the National Institutes of Health (NIH Grant Nos. K08 NS02048-04, AI058979, and NSO46478). The U.S. government has certain rights in this invention.

BACKGROUND OF THE INVENTION

Infectious agents of prion diseases, such as Creutzfeldt Jakob Disease (CJD), are devoid of nucleic acid and instead are composed of a specific infectious protein (Prusiner (1982) *Science* 216:136-44). This protein, PrP$^{Sc}$, appears to be generated by the template-induced conformational change of a normally expressed neuronal glycoprotein, PrP$^C$ during the course of disease (Prusiner, S. B. (ed.) *Prion Biology and Diseases*, Cold Spring Harbor Laboratory Press, Cold Spring Harbor, N.Y. (1999). While numerous studies have established the conversion of PrP$^C$ to PrP$^{Sc}$ as the central pathogenic event of prion disease, cellular factors other than PrP$^C$ which may be involved in the efficient catalysis of PrP$^{Sc}$ are unknown (Aguzzi and Weissmann *Nature* 389:795-8).

Various methods have been developed to enhance the amplification of PrP$^{Sc}$ to increase the sensitivity of detecting PrP$^{Sc}$. Saborio, et al. ((2001) *Nature* 411:810-3) disclose the use of a protein misfolding cyclic amplification (PMCA) method wherein prion-infected tissue homogenates containing PrP$^c$ are combined with normal brain homogenates in the presence of TRITON® X-100 and sodium dodecyl sulfate and subjected to repeated cycles of incubation and sonication to convert PrP$^c$ in normal tissue to PrP$^{Sc}$. Lucassen, et al. ((2003) *Biochemistry* 42:4127-35) disclose a modified version of the PMCA method wherein the normal and prion-infected tissue homogenates are incubated under non-denaturing conditions for the conversion of PrP$^C$ in normal tissue to PrP$^{Sc}$. Further, purified proteins and cell-lysate systems have been used to convert PrP$^C$ to PrP$^{Sc}$ (Caughey et al. (2000) *Curr Issues Mol Biol* 2(3):95-101; Horiuchi and Caughey (1999) Structure Fold Des. 7:R231-R240; Saborio et al. (1999) *Biochem Biophys Res Commun* 258:470-475). Optimal non-denaturing, cell-free conditions (KCl, MgCl$_2$, citrate buffer and sarkosyl) for the conversion of PrP$^C$ to PrP$^{Sc}$ have also been disclosed (Horiuchi and Caughey (1999) *EMBO J.* 18:3193-3203). Cordeiro, et al. ((2001) *J. Biol. Chem.* 276:49400-9) teach that sequence-specific DNA binding to recombinant murine prion protein converts it from PrP$^C$ to the soluble PrP$^{Sc}$ isoform similar to that found in the fibrillar state. Further, Nandi et al. ((2002) *Biochemistry* 41:11017-11024) teach that the interaction between PrP$^c$ and anions (sulfate/phosphate) in polyionic ligands such as sulfated glycosaminoglycan and DNA, induce unfolding of the prion protein and conversion to PrP$^{Sc}$. DebBurman, et al. ((1997) *Proc. Natl. Acad. Sci. USA* 94(25):13938-43) demonstrate that GroEL and Hsp104 (heat shock protein 104), significantly, but distinctly affect conversion of PrP$^C$ to PrP$^{Sc}$.

Similarly, nucleic acids have been shown to bind to and promote the conformational change of recombinant PrP (Derrington, et al. (2002) *C R Biologies* 325:17-23; Moscardini, et al. (2002) *J. Mol. Biol.* 318:149-59; Gabus, et al. (2001) *J. Biol. Chem.* 276:19301-9; Gabus, et al. (2001) *J. Mol. Biol.* 307:1011-21; Proske, et al. (2002) *Chembiochem* 3:717-25; Weiss, et al. (1997) *J. Virol.* 71:8790-7; Zeiler, et al. (2003) *Biotechnol. Appl. Biochem.* 37:173-82; Nandi, et al. (2002) *J. Mol. Biol.* 322:153-61; Brimacombe, et al. (1999) *Biochem. J.* 342:605-613).

Purified PrP$^C$ also converts into protease-resistant PrP$^{Sc}$ in vitro in the absence of cellular cofactors (Kocisko, et al. (1995) *Nature* 370:471-4) and, thus, the PrP molecules themselves are sufficient to drive species-and strain-specific PrP$^{Sc}$ formation in vitro (Bessen, et al. (1995) *Nature* 375:698-700; Kocisko, et al. (1995) *Proc. Natl. Acad. Sci. USA* 92:3923-7). However, a 50-fold molar excess of purified PrP$^{Sc}$ is required to drive conversion of purified PrP$^C$, suggesting that optimal efficiency of amplification may depend on the presence of cellular factors other than PrP$^C$ (Caughey, et al. (1999) *Methods Enzymol.* 309:122-33). Transgenic experiments in mice and cultured cells also suggest that prion formation requires a catalytic factor "X" that has high affinity for positively charged residues at the C- and N-termini of PrP (Telling, et al. (1995) *Cell* 83:79-90; Kanecko, et al. (1997) *Proc. Natl. Acad. Sci. USA* 94:10069-74; Zulianello, et al. (2000) *J. Virol.* 74:4351-60; Perrier, et al. (2002) *Proc. Natl. Acad. Sci. USA* 99:13079-84).

While PrP$^{Sc}$ detection limits of 2 pM, corresponding to an aggregate concentration of approximately 2 fM (Bieschke, et al. (2000) *Proc. Natl. Acad. Sci. USA* 97(10):5468-73) to 50 pg PrP$^{Sc}$ (Barnard, et al. (2000) *Luminescence* 15: 357-362) have been reported using immunoassays, improved methods of increasing the detection limits are needed to enhance the detection limits of these assays so that prion diseases may be detected at the earliest possible stages of development. It has now been found that amplification of PrP$^{Sc}$ in vitro can be enhanced using RNA, synthetic polyanions and partially purified substrates thereby increasing the sensitivity of diagnostic methods for detecting PrP$^{Sc}$.

SUMMARY OF THE INVENTION

The present invention is a method for purifying PrP$^C$. The purification method of the invention involves separating a protein sample containing PrP$^C$ by PrP$^C$-specific immunoaffinity chromatography, and separating the eluate of the immunoaffinity chromatography step by ion exchange chromatography so that a substantially purified preparation of PrP$^C$ is obtained.

The present invention further includes a substantially purified preparation of PrP$^C$ obtained by immunoaffinity chromatography and/or exchange chromatography. The present invention also includes methods and kits for identifying the presence of PrP$^C$ using the purified preparation of PrP$^C$.

DETAILED DESCRIPTION OF THE INVENTION

It has been shown that a modified version of the PMCA method can be used to amplify PrP$^{Sc}$ in vitro without sonication or SDS in a species- and strain-specific manner (Lucassen, et al. (2003) supra). In this method, diluted prion-infected brain homogenate (0.1% w/v) is mixed either with 5% (w/v) normal brain homogenate (relative ratio 1:50) or buffer control and incubated overnight at 37° C. Hamster Sc237 PrP$^{Sc}$ is typically amplified ~6-fold under these conditions. It has now been found that, under similar PrP$^{Sc}$ amplification reactions, treatment of homogenate with DNase-free pancreatic RNase abolishes PrP$^{Sc}$ amplification in a dose-dependent manner. In vitro PrP$^{Sc}$ amplification was also abolished by purified RNase A, which degrades RNA through cleavage at pyrimidine residues (Volkin and Cohn (1953) *J. Biol. Chem.* 205:767), and by RNase T1, which specifically cleaves RNA molecules at guanine residues (Sato-Asano (1959) *J. Biochem.* (Tokyo) 46:31). Non-specific nucleases such as micrococcal nuclease and benzonase also inhibited PrP$^{Sc}$ amplification.

In contrast, PrP$^{Sc}$ amplification was not affected by addition of RNase V1, which degrades double-stranded RNA molecules (Lockard and Kumar (1981) *Nucl. Acids Res.* 9:5125-40) or RNase H, which specifically cleaves RNA:DNA hybrids (Banks (1974) *Euro. J. Biochem.* 47:499-507). These results indicate that a nucleic acid molecule, such as a single-stranded RNA, is involved in the amplification of PrP$^{Sc}$ in vitro using brain homogenate. Addition of DNase or the restriction enzyme EcoRI did not decrease PrP$^{Sc}$ amplification, indicating that DNA is not required for this process. Addition of apyrase and heparinase III also had no effect on PrP$^{Sc}$ amplification, indicating that neither of these high-energy nucleotides nor molecules containing heparan sulfate are required for PrP$^{Sc}$ amplification in vitro.

Levels of PrP$^{C}$ and PrP$^{Sc}$ were measured after an overnight incubation with the various nuclease preparations to determine whether the nuclease preparations were contaminated with proteases. These measurements confirmed that levels of PrP$^{C}$ and input PrP$^{Sc}$ were both unperturbed by addition of enzymes that inhibited PrP$^{Sc}$ amplification.

As a control to confirm that abolition of PrP$^{Sc}$ amplification was dependent upon catalytic activity of each inhibitory nuclease, benzonase, micrococcal nuclease and RNase A were added to PrP$^{Sc}$ amplification reactions in an enzymatically inactive state. Both benzonase and micrococcal nuclease require divalent cations for enzymatic activity, thus these nucleases were inactivated by the addition of 5 mM EDTA. The active site of RNase A contains a critical histidine residue that is covalently modified by diethyl pyrocarbonate (DEPC). Therefore, RNase A was pretreated with DEPC to inhibit the ribonuclease activity of eNase A. Excess DEPC was subsequently removed by dialysis. The results of these experiments indicated that none of the three nucleases inhibited PrP$^{Sc}$ amplification in their inactive states and that intact RNA molecules catalyze this process in brain homogenates.

Both RNase A and RNase T1 cleave RNA by a chemical mechanism involving the formation of a 2',3'-cyclic phosphate intermediate. RNase A digestion ultimately generates pyrimidine 3'-monophosphate products (Volkin and Cohn (1953) supra), while RNase T1 digestion yields 2',3'-cyclic guanosine monophosphate (GMP) end-products (Sato-Asano (1959) supra). The effect of cyclic 2',3'-GMP and 3'-cytidine monophosphate (CMP) on PrP$^{Sc}$ amplification were measured to ascertain whether the inhibitory effect of the RNase enzymes was attributable to inhibition by accumulated end-products. Neither of these nucleotides inhibited PrP$^{Sc}$ amplification in vitro at concentrations up to 1 mM. Control experiments negated the possibilities that contaminating proteases, steric hindrance, or digestion of end-products accounted for the inhibition of PrP$^{Sc}$ amplification by specific nucleases. Thus, RNA is involved in PrP$^{Sc}$ amplification in vitro in brain homogenates.

Isolated RNA molecules were analyzed for the ability to amplify PrP$^{Sc}$ from nuclease-treated normal brain homogenates. Total RNA isolated from hamster brain successfully reconstituted the ability of benzonase-pretreated brain homogenate to amplify PrP$^{Sc}$ in a dose-dependent manner. In contrast, purified heparan sulfate proteoglycan failed to reconstitute PrP$^{Sc}$ amplification using brain homogenates. Other polyanions, such as single-stranded DNA, polyadenylic acid, and polyglutamic acid also failed to reconstitute PrP$^{Sc}$ amplification using brain homogenates.

The molecular size of the RNA species which enhances PrP$^{Sc}$ amplification in brain homogenates was determined by fractionating a preparation of total hamster brain RNA by ultrafiltration through a filter with a molecular weight cutoff ~100,000. Using agarose gel electrophoresis, it was determined that the ribosomal RNA (rRNA) bands were observed in the retentate and the transfer RNA (rRNA) in the filtrate. Using these samples, it was found that the filter retentate, but not the filtrate, enhanced PrP$^{Sc}$ amplification. In similar experiments, total RNA was separated using oligo dT column chromatography and sucrose gradient separation. RNA which enhanced PrP$^{Sc}$ amplification was primarily found in the poly(A)$^-$ fraction from the oligo dT column chromatography and, upon size separation by sucrose gradient, was determined to be ~1.49 kb in size; however, the RNA molecule did not appear to be a ribosomal RNA subunit. These data indicate that the RNA species which catalyzes PrP$^{Sc}$ amplification or conversion in brain homogenate is greater than 100,000 molecular weight (>300 nucleotides).

In reconstitution experiments, nuclease pretreatment of endogenous RNA was incomplete because these digestion reactions were carried out at 4° C. to avoid denaturing PrP$^{C}$ prior to the addition of polyanions. Thus, it was determined whether the addition of total hamster brain RNA could increase the efficiency of PrP$^{Sc}$ amplification in vitro in brain samples which were not pretreated with nuclease. In these studies, a more dilute homogenate of prion-infected brain (0.02% w/v) was mixed overnight with 5% (w/v) normal brain homogenate (relative ratio 1:250) without sonication and PrP$^{Sc}$ amplification was subsequently measured. These results indicated that addition of total hamster brain RNA to this mixture of intact brain homogenates significantly stimulated PrP$^{Sc}$ amplification over baseline. As a control, input PrP$^{Sc}$ or PrP$^{C}$ in these samples was measured to confirm that addition of RNA did not alter the levels of PrP$^{Sc}$ or PrP$^{C}$.

Specificity of RNA-mediated stimulation of PrP$^{Sc}$ amplification was determined by isolating total RNA from several sources, including *E. coli, S. cerevisiae, C. elegans, D. melanogaster*, and mouse and hamster brain. Agarose gel electrophoresis analysis of these preparations revealed the expected band patterns for each species and confirmed that each preparation contained high-quality, non-degraded RNA. Furthermore, each of these preparations was substantially free from contaminants as judged by optical spectroscopy ($OD_{260}/OD_{280}$>1.9). Unexpectedly, among the preparations of RNA tested, only hamster and mouse brain RNA stimulated PrP$^{Sc}$ amplification in vitro. This species-specificity was not attributed to tissue-specificity because total hamster liver RNA also stimulated PrP$^{Sc}$ amplification. Thus, mice and hamsters express specific RNA molecules involved in PrP$^{Sc}$ amplification.

The utility of supplementing a standard amplification method with RNA was determined; PrP$^{Sc}$ was amplified by the PMCA technique (Saborio, et al. (2001) supra) in the presence and absence of supplemental RNA. These results showed that addition of total hamster brain RNA increased the PrP$^{Sc}$ signal obtained by eight sonication cycles of PMCA by ~10-fold, and that more PrP$^{Sc}$ was detected at every sonication cycle when additional RNA was present.

Because brain homogenates may contain stimulatory molecules as well as inhibitory molecules and post-translational modifications of PrP$^{C}$ might affect its ability to convert efficiently to PrP$^{Sc}$, the mature form of mammalian PrP$^C$ was purified directly from normal brain tissue using detergent solubilization (Nishina, et al. (2004) *Biochemistry* 43:2613-2621). To ensure that the results did not depend upon any peculiarities of one purification method, two different protocols were developed to generate PrP$^C$ molecules capable of undergoing efficient conversion to PrP$^{Sc}$. In the first protocol, adapted from the method of Pan, et al. (Pan, et al. (1993) *Proc. Natl. Acad. Sci. USA* 90:10962-10966; Pan, et al. (1992) *Protein Sci.* 1:1343-1352), PrP$^C$ molecules were purified from solubilized brain membranes by sequential adsorption to copper and lectin affinity columns. This procedure produced a preparation that contained conversion-competent PrP$^C$ molecules, but also contained many contaminating proteins, resulting in <10% purity. In the second protocol, PrP$^C$ was immunopurified using immobilized anti-PrP antibodies. This procedure generated samples containing PrP$^C$ with ~50% purity; one major contaminant was identified as the immunoglobulin heavy chain. The partially purified PrP$^C$ molecule contained intact Asn-linked polysaccharide and C-terminus-linked glycophosphatidylinositol post-translational modifications. The three glycoforms of PrP$^C$ were identifiable as bands with molecular masses in the range from 30 to 33 kDa. These bands were more abundant in a sample purified from Tga20 transgenic PrP-overexpressing mice and absent from a sample prepared from Prnp$^{0/0}$ mice.

A preparation of immunopurified hamster PrP$^C$ was incubated overnight with purified Syrian hamster Sc237 PrP27-30 template at a molar ratio of 250:1, and Prp$^{Sc}$ amplification was measured. Co-incubation of these two purified prion proteins alone yielded ~2-fold amplification of PrP$^{Sc}$. Addition of Prnp$^{0/0}$ mouse brain homogenate lacking PrP$^C$ to the mixture of purified proteins increased the PrP$^{Sc}$ amplification level to ~10-fold, similar to the level of PrP$^{Sc}$ amplification in crude brain homogenates (Lucassen, et al. (2003) supra). In control reactions, Prnp$^{0/0}$ brain homogenate did not affect the protease resistance of either PrP$^C$ or PrP27-30 molecules in isolation. These results confirm that crude brain homogenates contain one or more cofactor(s) that promote the efficiency of PrP$^{Sc}$ amplification.

It was subsequently determined whether isolated RNA molecules could stimulate PrP$^{Sc}$ amplification from the purified prion proteins. The addition of total hamster liver RNA to a mixture of PrP27-30 and immunopurified PrP$^C$ molecules yielded ~10-fold PrP$^{Sc}$ amplification as compared to samples lacking RNA. This result indicates that RNA molecules can act directly upon prion proteins without intermediary molecules and that purified PrP$^C$, PrP$^{Sc}$, and RNA molecules are sufficient to reconstitute PrP$^{Sc}$ amplification to the same level as crude brain homogenates. The efficiency of PrP$^{Sc}$ amplification stimulated by RNA was further increased by protein-misfolding cyclic amplification (Saborio, et al. (2001) supra), resulting in >20-fold total PrP$^{Sc}$ amplification after 24 cycles, which again was similar to the level of PrP$^{Sc}$ amplification obtained with protein-misfolding cyclic amplification using reconstituted brain homogenate.

Using crude brain homogenates, RNA concentrations between 100 and 500 μg/ml stimulate PrP$^{Sc}$ amplification in a species-specific manner. To study the species specificity and potency of RNA stimulation using purified substrate, the ability of varying concentrations of total RNA prepared from a variety of species to stimulate PrP$^{Sc}$ amplification was analyzed. Unexpectedly, it was found that total RNA prepared from every species tested, including *C. elegans* and *E. coli*, potently stimulated PrP$^{Sc}$ amplification using purified substrate. For each preparation, the threshold RNA concentration for stimulation of PrP$^{Sc}$ amplification was ~1 μg/ml, and stimulation was optimal at an RNA concentration of ~10 μg/ml. In contrast, the threshold concentration of total hamster liver RNA required to stimulate PrP$^{Sc}$ amplification in crude homogenates was ~100 μg/ml, and the concentration required for optimal stimulation was ~500 μg/ml. Thus, RNA stimulation of PrP$^{Sc}$ amplification was both more potent and less specific using the purified substrate than homogenate mixtures.

These results indicated that a specific RNA species may not have been uniquely responsible for stimulating PrP$^{Sc}$ amplification. Thus, the potencies of poly(A)$^+$ and poly(A)$^-$ RNA for stimulation of PrP$^{Sc}$ amplification was determined. The results indicated that, despite ~100-fold enrichment of mRNA molecules in the poly(A)$^+$ fraction compared with the poly(A)$^-$ fraction, the two preparations stimulated PrP$^{Sc}$ amplification with purified substrate with equal potency. In addition, no differences in stimulation potency between brain and liver total RNA were observed, indicating that stimulatory RNA molecules were not specifically enriched in brain tissue.

These results indicated that polyanions could stimulate PrP$^{Sc}$ amplification, and therefore a variety of pure compounds were tested for their ability to stimulate Prp$^{Sc}$ amplification using purified substrate. Several commercially available preparations of synthetic homopolymeric nucleotides with overlapping size distributions were assayed. Among the compounds tested, poly(A) and poly(dT) stimulated PrP$^{Sc}$ amplification at a concentration of 1 μg/ml; poly(dA) stimulated PRP$^{Sc}$ amplification at a concentration of 100 μg/ml; and poly(C) failed to stimulate PrP$^{Sc}$ amplification at all concentrations tested (0.001 to 100 μg/ml) . Double-stranded plasmid DNA also stimulated amplification at a concentration of ~10 μg/ml. Taken together, these results indicate that RNA, single-stranded DNA, and double-stranded DNA molecules can stimulate PrP$^{Sc}$ amplification and that homopolymeric nucleotide preparations with overlapping size distributions differ in their ability to stimulate PrP$^{Sc}$ amplification, according to the rank order poly(A)=poly(dT)>poly(da)>poly(C).

To study in isolation the effect of polynucleotide size upon stimulatory activity, discrete size fractions of poly(A) were tested for their ability to stimulate PrP$^{Sc}$ amplification using purified substrate. The results indicated that poly(A) oligonucleotides≦45 bases in length were unable to stimulate PrP$^{Sc}$ amplification; a fraction containing poly(A) polymers between 0.2 and 0.4 kb in length partially stimulated PrP$^{Sc}$ amplification; and poly(A) polymers>4 kb in length strongly stimulated PrP$^{Sc}$ amplification. Furthermore, monomeric nucleotides did not stimulate PrP$^{Sc}$ amplification at concentrations between 1 ng/ml and 100 μg/ml. Taken together, these results indicate that the threshold size required for stimulation of PrP$^{Sc}$ amplification by poly(A) was ~300 bases. Consistent with this estimate of threshold size, a uniform preparation of poly(G)-containing polymers ~0.2 kb in length did not stimulate PrP$^{Sc}$ amplification, whereas a preparation of poly(U)-containing polymers 0.39 kb in length potently stimulated PrP$^{Sc}$ amplification.

Several independent lines of investigation have implicated proteoglycans and glycosaminoglycans, particularly heparin sulfate proteoglycan (HSPG), in the pathogenesis of prion diseases (Caughey & Raymond (1993) *J. Virol.* 67:643-650; Shaked, et al. (2001) *J. Biol. Chem.* 276:14324-14328; Ben-Zaken, et al. (2003) *J. Biol. Chem.* 278:40041-40049), and it has been shown that heparan sulfate and pentosan sulfate stimulate cell-free conversion of radiolabeled PrP (Wong, et al. (2001) *EMBO J.* 20:377-386). Therefore, heparan sulfate (molecular mass, ~12-14 kDa), pentosan sulfate, and HSPG (molecular mass, >400 kDa) were tested for their ability to stimulate PrP$^{Sc}$ amplification. Pentosan sulfate and HSPG stimulated PrP$^{Sc}$ amplification only moderately at a concentration of 100 µg/ml, whereas heparan sulfate had no effect. The prior art has shown that copper affects the affinity of heparin binding to PrP (Warner, et al. (2002) J. Biol. Chem. 277:18421-18430), and therefore heparan sulfate stimulation of PrP$^{Sc}$ amplification was also measured in the presence of copper. No apparent stimulation of PrP$^{Sc}$ amplification by heparan sulfate was observed in the presence of 1-100 µM CuCl$_2$. The levels of stimulation induced by pentosan sulfate and HSPG were both <30% the level of control stimulation by total hamster liver RNA. An artificial polyanionic compound, polyglutamate (molecular mass ~50-100 kDa), also stimulated PrP$^{Sc}$ amplification over a broad range of concentrations from 0.1 to 100 µg/ml. However, the level of stimulation induced by polyglutamate was again less than the level of control stimulation induced by total hamster RNA, and some of the apparent increase in PrP$^{Sc}$ signal caused by polyglutamate may have been attributable to a direct effect of this compound on the inherent protease resistance of PrP27-30.

Studies have suggested a role for charged lipids in PrP structural conversion (Sanghera & Pinheiro (2002) J. Mol. Biol. 315:1241-1256). Therefore, it was determined whether an extract of brain gangliosides could stimulate PrP$^{Sc}$ amplification in vitro. The results showed that brain gangliosides did not affect the efficiency of PrP$^{Sc}$ amplification using purified substrate. Detailed analytical studies have shown that purified prion rods contain a glycogen-like scaffold composed primarily of 1,4-linked glucose units (Appel, et al. (1999) Biol. Chem. 380:1295-1306). Therefore, it was determined whether glycogen could stimulate PrP$^{Sc}$ amplification. This compound also did not stimulate the formation of PrP$^{Sc}$.

During immunoaffinity purification of PrP$^C$, it was unexpectedly found that subjecting preparation the purified preparation to a desalting buffer exchange column diminished its capacity to amplify PrP$^{Sc}$ molecules in vitro despite full recovery of PrP$^C$ molecules in the desalted preparation (preparation "X"). Reconstitution was used to test the possibility that the diminished ability of preparation "X" to amplify PrP$^{Sc}$ molecules in vitro was specifically caused by removal of imidazole. Indeed, re-addition of 50 mM imidazole to preparation "X" restored the ability of this preparation to serve as a substrate for PrP$^{Sc}$ amplification. Also, addition of 5 mM imidazole restored PrP$^{Sc}$ amplification, whereas 250 mM imidazole inhibited PrP$^{Sc}$ amplification.

Because imidazole is known to bind to divalent metal ions, it was determined whether imidazole's ability to stimulate PrP$^{Sc}$ amplification may have been due to the presence of metal ions in preparation "X". Thus, several methods were used to remove metal ions from "X", and the resulting preparations were assayed for the effects of imidazole on PrP$^{Sc}$ amplification. The results indicated that dialysis of "X" for 16 hours at 4° C. was not sufficient to render PrP$^{Sc}$ amplification imidazole-sensitive (preparation "Y"), whereas applying immunopurified PrP$^C$ to an uncharged chelating SEPHAROSE™ resin generated a flow-through fraction which was able to amplify PrP$^{Sc}$ in the absence of imidazole (preparation "Z"). It was subsequently determined whether the source of inhibitory metal ions in preparation "X" might be Cu$^{2+}$ ions that leached from the immobilized Cu$^{2+}$ affinity column. To investigate this possibility, a desalting buffer exchange column was substituted for the immobilized Cu$^{2+}$ affinity step to generate a substrate prepared entirely with reagents free of exogenous metals. The buffer-exchanged substrate remained imidazole-sensitive, indicating that at least a fraction of the inhibitory metal ions originated from the brain tissue source. Subjecting the buffer-exchanged preparation to an extra cation exchange chromatography step yielded highly purified PrP$^C$ molecules (>98% by silver stain), which were imidazole-insensitive, presumably because the additional purification step efficiently removed metal ions derived from the original brain tissue. Because the combination of immunoaffinity and ion exchange chromatography offered several advantages, i.e., high purity, consistent yield, and the use of metal-free reagents, this protocol was used to purify substrate PrP$^C$ molecules for subsequent experiments characterizing the effects of divalent metal ions on Prp$^{Sc}$ amplification.

Using purified, imidazole-insensitive PrP$^C$ substrate, the effects of CuCl$_2$ and chelating compounds on PrP$^{Sc}$ amplification was characterized in the presence and absence of poly (A) RNA. The results indicate that CuCl$_2$ potently inhibited PrP$^{Sc}$ amplification with an IC$_{50}$ ~1 µM, both in the presence and absence of RNA. PrP$^{Sc}$ amplification was not influenced by addition of the chelating compounds EDTA or neocuproine, confirming the absence of free Cu$^{2+}$ ions in the purified substrate preparation and other assay reagents. Control samples showed that addition of 100 µM CuCl$_2$ did not affect the quantity or protease-resistance of input PrP$^C$ or PrP$^{Sc}$ molecules by themselves.

The specificity of inhibition among various divalent metal compounds was analyzed and it was found that ZnCl$_2$ inhibited PrP$^{Sc}$ amplification with an IC$_{50}$ ~10 µM. In contrast, neither MnCl$_2$ nor CoCl$_2$ affected PrP$^{Sc}$ amplification at concentrations up to 100 µM. In control samples, none of the metal compounds tested affected the quantity or protease-resistance of input PrP$^C$ molecules in the absence of PrP$^{Sc}$ template. Previous studies indicated that recombinant PrP molecules have similar affinities for CU$^{2+}$ and Mn$^{2+}$ ions (Brown, et al. (2000) EMBO J. 19:1180-1186), and that PrP$^{Sc}$ molecules formed during the course of prion disease preferentially bind Mn$^{2+}$ ions (Wong, et al. (2001) supra; Thackray, et al. (2002) Biochem J 362:253-258). Therefore, the lack of inhibition by MnCl$_2$ was investigated in greater detail by testing whether pre-addition of 1-100 µM MnCl$_2$ could prevent CuCl$_2$-mediated inhibition of PrP$^{Sc}$ amplification. The results showed that MnCl$_2$ did not influence the potency of CuCl$_2$-mediated inhibition indicating that, even when present at 1000-fold molar excess, Mn$^{2+}$ ions cannot compete with Cu$^{2+}$ ions for the specific binding sites that mediate metal-induced inhibition of PrP$^{Sc}$ amplification.

It was subsequently determined whether inhibition of PrP$^{Sc}$ amplification by CuCl$_2$ could be reversed by addition of EDTA or imidazole. The results showed that addition of 4 mM EDTA or 50 mM imidazole prior to addition of 1 µM CuCl$_2$ prevented inhibition of PrP$^{Sc}$ amplification. In contrast, addition of EDTA or imidazole shortly after addition of CuCl$_2$ failed to rescue PrP$^{Sc}$ amplification, indicating that the inhibitory effect of 1 µM CuCl$_2$ was not readily reversible.

The inhibition of PrP$^{Sc}$ amplification by Cu$^{2+}$ ions could be mediated either by inhibition of PrP$^C$/PrP$^{Sc}$ binding or by a conformational mechanism, such as stabilization of PrP$^C$ structure. To distinguish between these possibilities, the effect of CuCl$_2$ on PrP$^C$/PrP$^{Sc}$ binding was directly investigated by using an ultracentrifugation assay. The samples were incubated at 4° C. during binding to prevent PrP$^C$ conversion to PrP$^{Sc}$ (Lucassen, et al. (2003) Biochemistry 42:4127-4135). PrP$^C$/PrP$^{Sc}$ binding, as determined as the ratio of PrP$^C$ to PrP27-30 in the pellet, increased from 0.29 to 0.46 with addition of CuCl$_2$. These results indicate that addition of CuCl$_2$ does not inhibit PrP$^C$/PrP$^{Sc}$ binding, and therefore indicates that a conformational mechanism is likely responsible for the CuCl$_2$-mediated inhibition of PrP$^{Sc}$ amplification.

To further demonstrate that the preparation of substantially purified PrP$^C$ was a competent substrate for PrP$^{Sc}$ amplification and autocatalysis, serial propagation experiments were performed using immunopurified PrP$^C$ molecules and purified PrP$^{Sc}$ molecules derived from two different hamster prion strains as reaction substrates. PrP$^C$ molecules were incubated with PrP27-30 molecules (proteinase K-treated, purified PrP$^{Sc}$ molecules originally derived from either Sc237 or 139H hamster scrapie strains), and subjected to intermittent 30 second cycles of indirect sonication every 30 minutes. After each 24 hour incubation period, 20 µl of the reacted sample was used to seed the next 200 µl reaction volume and this entire process was repeated 16 times, resulting in an overall 10$^{16}$-fold dilution of input PrP$^{Sc}$. With the exception of a control sample (250 ng/ml PrP$^C$ substrate), the remaining samples were subsequently subjected to digestion with 50 µg/ml proteinase K for 1 hour at 37° C., and PrP molecules were detected by western blot analysis. The results showed that PrP$^{Sc}$ molecules from both strains successfully propagated their protease-resistant conformation in vitro through the entire course of the experiment. Inclusion of synthetic poly(A) RNA (10 µg/ml) stimulated the propagation process, since control samples lacking poly(A) RNA failed to propagate the PrP$^{Sc}$ conformation during the experiment. These results obtained in a purified system show that naturally expressed, purified PrP molecules are capable of autocatalytic conformational change. Moreover, it was observed that all of the PrP$^C$ substrate in the reaction was converted into PrP$^{Sc}$ after 24 hours of PMCA, resulting in ~5000-fold amplification of the starting PrP$^{Sc}$ template in 24 hours PMCA.

Having achieved an enhanced stimulation of PrP$^{Sc}$ conversion from PrP$^C$, the present invention embraces a nucleic acid molecule which enhances, increases, or stimulates the amplification of PrP$^{Sc}$ as compared to a control, e.g., the amplification of PrP$^{Sc}$ in the absence of the nucleic acid molecule. Enhancing, increasing, or stimulating PrP$^{Sc}$ amplification is intended to mean that, when compared to a control, more PrP$^{Sc}$ molecules are produced in a specified amount of time or a shorter amount of time is needed to produce a specified amount of PrP$^{Sc}$ molecules. As used in the context of the present invention, the term "a nucleic acid molecule" is intended to include one or more single- or double-stranded DNA or RNA molecules which enhance the amplification of PrP$^{Sc}$. In one embodiment, the molecule is a single-stranded nucleic acid molecule. In another embodiment, the molecule is not an RNA molecule. In a further embodiment, the molecule is homopolymeric (e.g., poly(A), poly (dT), etc). Not wishing to be bound by theory, it is believed that optimal stimulation of PrP conversion requires the nucleic acid to adopt a particular surface or three-dimensional structure; one which cannot be obtained by poly(c). Unlike other homopolymer polynucleotides, it is well-known that poly(C) does not easily acquire a secondary structure (Ansevin, et al. (1975) *J. Biol. Chem.* 250:281-289). Thus, a further embodiment embraces a homopolymeric nucleic acid molecule which is not poly(C).

The size fractionation experiments disclosed herein indicate that a minimum molecular size of ~300 bases is required for full stimulation activity. It is contemplated that while small polyanionic compounds and polycationic dendrimers block prion propagation, large polyanionic nucleic acid molecules, e.g., more than 300 nucleotides, may disaggregate prion rods thereby increasing the number of infectious particles available to drive conversion. Therefore, in particular embodiments, the nucleic acid molecule of the present invention is at least 300 nucleotides in length.

The nucleic acid molecule of the present invention can be purified using any standard nucleic acid isolation method or the nucleic acid molecule can be a component of a complex mixture of molecules. Moreover, the instant nucleic acid molecule can be obtained from a natural source or synthesized. When obtained from a natural source, the source is preferably a vertebrate including mammals such as humans, bovine, ovine, felines, canines, deer, elk, mice, hamsters, mink and the like. Other vertebrates from which the molecule can be obtained include fish or birds. When synthesized, the nucleic acid molecule can be generated from a template such as a genomic DNA or cDNA template by in vitro, in situ, or in vivo transcription, replication or PCR, or alternatively, the molecule can be produced using an automated nucleic acid synthesizer. The molecule can be the entire molecule or an active fragment thereof which retains the capacity for enhancing the amplification of PrP$^{Sc}$.

If synthesized, the nucleic molecule can contain a modified backbone or non-natural internucleoside linkages to increase stability or decrease degradation. For example, an RNA-based molecule can have a modified backbone which contains phosphorothioates, chiral phosphorothioates, phosphorodithioates, phosphotriesters, aminoalkylphosphotriesters, methyl and other alkyl phosphonates, short chain alkyl or cycloalkyl internucleoside linkages, mixed heteroatom and alkyl or cycloalkyl internucleoside linkages, or one or more short chain heteroatomic or heterocyclic internucleoside linkages and the like. Alternatively, the RNA molecule can be have both the sugar and the internucleoside linkage, i.e., the backbone, of the nucleotide units replaced with novel groups (e.g., a peptide nucleic acid (PNA)). Other such modifications which increase the stability or decrease the degradation of RNA are well-known to those of skill in the art.

PrP$^C$, as used herein, is defined as the naturally expressed glycoprotein PrP$^C$, also known as PrP-sen, which is found in the neurons of mammals. Not to be held to any particular mechanism of action, it is believed that contact between PrP$^C$ and an infectious prion or PrP$^{Sc}$ brings about a conformational change in PrPC, converting it from a protein primarily composed of alpha-helices to a protein primarily composed of beta-sheets. This conversion creates a protease resistant, prion protein (i.e., PrP$^{Sc}$, PrP-res) associated with a prion disease. While the presence of PrP$^{Sc}$ is correlated with a prion-associated disease, the skilled artisan can appreciate that PrP$^{Sc}$ may or may not be the causative agent of a prion-associated disease. Hence, the term "infectious prion" is intended to mean a prion which causes a prion-associated disease. Moreover, as is readily apparent to the skilled artisan, naturally expressed glycoprotein PrP$^C$, PrP$^{Sc}$, and infectious prion are distinct from recombinantly produced prion proteins which have not been shown in in vivo model systems to be associated with a prion disease.

To facilitate the diagnosis of a prion-associated disease, the present invention also embraces a method for identifying the presence of PrP$^{Sc}$ in a sample by enhancing the amplification of PrP$^{Sc}$ and identifying the presence of PrP$^{Sc}$. The method involves contacting a sample suspected of containing an infectious prion protein with a nucleic acid molecule which enhances the amplification of PrP$^{Sc}$. In this step of the method, PrP$^{Sc}$ can be converted from PrP$^C$ which is endogenous to the sample and has yet to be converted to PrP$^{Sc}$ or can be supplied exogenously as a substantially purified or isolated protein, mixture of proteins, or homogenate.

In particular embodiments, PrP$^C$ is provided in the method as a substantially purified protein. As used herein, the term substantially purified is intended to mean that at least 50%, 75%, 85%, 95%, or 98% of the protein in the PrP$^C$ preparation is PrP$^C$, as determined by, e.g., silver stain analysis of a polyacrylamide gel. In particular embodiments, at least 98% of the protein in the PrP$^C$ preparation is PrP$^C$. An exemplary method for preparing substantially purified PrP$^C$ includes separating a protein sample (e.g., brain homogenate) containing PrP$^C$ by PrP$^C$-specific immunoaffinity chromatography (i.e., a matrix containing an antibody which binds PrP$^C$), and separating the eluate of the immunoaffinity chromatography step by ion exchange chromatography (e.g., cation exchange chromatography).

A sample is intended to include biological material, e.g., blood, plasma, serum, cell products, cell extracts, cerebrospinal fluid (CSF), tissue homogenates, urine, semen, and combinations thereof as well as environmental materials, e.g., soil and water, and food samples including canned goods, meats, and animal fodder. A sample suspected of containing an infectious prion is one which may have come in contact with an infectious prion protein or one from an individual that may be predisposed (e.g., having inherited) or at risk of having or acquiring (e.g., ranchers) a prion-associated disease.

The nucleic acid molecule can be added in a solution to the sample or immobilized on a solid support such as a membrane or filter to which the sample is added. It is contemplated that the nucleic acid molecule can be provided in a kit and can be used alone or as a mixture, for example with other reagents which increase, enhance or stimulate the amplification of PrP$^{Sc}$. For example, the nucleic acid molecule can be combined with detergents such as TRITON® (X-100 or X-114), TWEEN® (e.g., 20 or 80), BRIJ®, GENAPOL®, CHAPS, CHAPSO ZWITTERGENT® (e.g., 3-16, 3-14, 3-12, 3-10, or 3-8), THESIT®, sarkosyl, deoxycholate (e.g., sodium deoxycholate, sodium taurodeoxycholate, or sodium glycodeoxycholate), NP-40, sodium dodecyl sulfate, digitonin, or cetyl-trimethylammonium bromide (CTAB); salts such as KCl, MgCl$_2$, or NaCl; buffers such as phosphate-buffered saline, tris-buffered saline, MOPS, HEPES, PIPES, Glycylglycine, MES or citrate buffer; chelating agents such as EDTA or EGTA; or other natural cofactors yet to be identified. In particular embodiments, a heterocyclic compound such as imidazole is employed for binding inhibitory divalent metals thereby increasing the intensity of PrP$^{Sc}$ amplification. Further examples are known by a person skilled in the art.

Further, the nucleic acid molecule can be used alone or in combination with other methodologies of amplifying PrP$^{Sc}$ thereby improving said method. For example, a nucleic acid molecule of the invention can be added to a homogenate of the methods of Saborio, et al. (2001) supra and Lucassen, et al. (2003) supra.

Moreover, factors such as temperature, ionic strength, pH-conditions, and the concentration of salt and non-ionic substances can be modified to further enhance the amplification of $PrP^{Sc}$ in the presence of the nucleic acid molecule.

The step of identifying $PrP^{Sc}$ can be carried out using one or more methods well-known to those skilled in the art. Assays which can be used for detecting, measuring, quantifying or analyzing the levels or presence or absence of $PrP^{Sc}$ include, but are not limited to, western blot analysis (e.g., Prionics®-Check WESTERN), immunocapillary electrophoresis (ICE), immunocytochemistry, enzyme-linked immunosorbent assay (e.g., the commercially available assay of Enfer Scientific Ltd.), conformation-dependent immunoassay (InPro Biotechnology, San Francisco, Calif.) or a sandwich immunoassay (e.g., the diagnostic test of the French Atomic Energy Commission) which use antibodies which specifically recognize $PrP^{Sc}$, as well as those disclosed in WO 02/057789; WO 02/033420; WO 02/082919; WO 02/093168; U.S. Pat. Nos. 6,524,809; 6,316,607; 6,261,790; 6,165,784 for example.

It is contemplated that the method of identifying $PrP^{Sc}$ will be useful in providing diagnostic or predictive information pertaining to the presence of infectious prions in the individual from whom the sample was obtained. This method can be used to diagnose natural or experimental transmissible spongiform encephalopathies (TSES) associated with infectious prions. TSEs which can be diagnosed include, but are not limited to, spongiform encephalopathy, feline spongiform encephalopathy, bovine spongiform encephalopathy (BSE), transmissible mink encephalopathy, scrapie, chronic wasting disease (CWD), sporadic Creutzfeldt-Jacob disease (CJD), iatrogenic CJD, variant CJD, atypical forms of CJD (e.g., ataxic CJD and Heidenhain's variant of CJD), kuru, Gerstmann-Sträussler-Scheinker disease, fatal familial insomnia, Alpers Syndrome or familial CJD.

The present invention further embraces a kit for identifying the presence of $PrP^{Sc}$. The kit includes a container holding one or more nucleic acid molecules of the invention which enhance the amplification of $PrP^{Sc}$ and instructions for using the nucleic acid molecule(s) for the purpose of amplifying $PrP^{Sc}$. The kit can further contain substantially purified $PrP^C$ as a substrate and/or a heterocyclic compound such as imidazole for binding inhibitory divalent metals. Moreover, the instant kit can be used in accordance with the method of the invention as well as in combination with well-known methods or assays for detecting the presence of $PrP^{Sc}$. Examples of containers include multi-well plates which allow simultaneous identification of $PrP^{Sc}$ in multiple samples.

As one of skill in the art will appreciate, the nucleic acid molecule, purified substrate and assay disclosed herein are useful for identifying therapeutic treatments of prion-associated diseases. Agents which target the nucleic acid molecule or $PrP^C/PrP^{Sc}$ complex to block or promote the interaction with $PrP^C$ are expected to modulate the conversion of $PrP^C$ to $PrP^{Sc}$ or an infectious prion. Thus, it is contemplated that the nucleic acid molecule can be used in binding studies or conversion assays with $PrP^C$ to screen for agents which block or promote the $PrP^C$-nucleic acid molecule interaction. A readout for a conversion assay can include the binding of an antibody specific for $PrP^{Sc}$, wherein increases in the amount or rate of $PrP^{Sc}$ production is indicative of a stimulatory agent whereas decreases in the amount or rate of $PrP^{Sc}$ production is indicative of an inhibitory agent.

An agent which increases, enhances or stimulates the interaction between a nucleic acid molecule and $PrP^C$, or the amount or rate of formation of $PrP^{Sc}$ produced, is useful in methods for enhancing the sensitivity of detecting $PrP^{Sc}$. An agent which decreases, inhibits or blocks the interaction between a nucleic acid molecule of the invention and $PrP^C$, or the amount or rate of formation of $PrP^{Sc}$ produced, is useful for treating or preventing a prion-associated disease (e.g. copper or zinc).

Such agents can be identified by screening a library of test agents. A library can comprise either collections of pure agents or collections of agent mixtures. Examples of pure agents include, but are not limited to, metal ions, proteins, polypeptides, peptides, nucleic acids, oligonucleotides, carbohydrates, lipids, synthetic or semi-synthetic chemicals, and purified natural products. Examples of agent mixtures include, but are not limited to, extracts of prokaryotic or eukaryotic cells and tissues, as well as fermentation broths and cell or tissue culture supernates. In the case of agent mixtures, one may not only identify those crude mixtures that possess the desired activity, but also monitor purification of the active component from the mixture for characterization and development as a therapeutic drug. In particular, the mixture so identified can be sequentially fractionated by methods commonly known to those skilled in the art which include, but are not limited to, precipitation, centrifugation, filtration, ultrafiltration, selective digestion, extraction, chromatography, electrophoresis or complex formation. Each resulting subfraction can be assayed for the desired activity using the original assay until a pure, biologically active agent is obtained.

Library screening can be performed in any format that allows rapid preparation and processing of multiple reactions such as in, for example, multi-well plates of the 96-well variety. Stock solutions of the agents as well as assay components are prepared manually and all subsequent pipetting, diluting, mixing, washing, incubating, sample readout and data collecting is done using commercially available robotic pipetting equipment, automated work stations, and analytical instruments for detecting the signal generated by the assay. Examples of such detectors include, but are not limited to, luminometers, spectrophotomers, calorimeters, and fluorimeters, and devices that measure the decay of radioisotopes.

Alternatively, inhibitory RNAs such as ribozymes, antisense RNA, RNAi, siRNA and the like can be designed to specifically interact with the nucleic acid molecule of the present invention to decrease the activity or expression of the nucleic acid molecule thereby decreasing its capacity to enhance the amplification of $PrP^{Sc}$. Inhibitory RNAs can be specific for sequences in the 5', 3' or middle of the RNA molecule. The target region can be selected experimentally or empirically. For example, siRNA target sites in a gene of interest may be 19-27 nucleotides in length, include an AA dinucleotide sequence at the 5' end and preferably have a G/C content of 30-50% (see, e.g., Elbashir, et al. (2001) *Nature* 411; 494-498).

As indicated above, inhibitory agents such as copper and zinc are useful in a method for inhibiting the conversion of $PrP^C$ to $PrP^{Sc}$. Such a method involves contacting a sample containing $PrP^{Sc}$ or suspected of containing $PrP^{Sc}$, e.g., blood, plasma, serum, cell products, etc. with an inhibitory agent such as copper or zinc thereby inhibiting the conversion of $PrP^C$ to $PrP^{Sc}$. Such a method is useful in the prevention or treatment of a prion-associated disease as well as analyzing the mechanism(s) involved in $PrP^{Sc}$ conversion in in vivo model systems.

As will be appreciated by the skilled artisan, a transgenic non-human animal can be produced which overexpresses a nucleic acid molecule of the present invention. Such a transgenic animal would be useful in methods of detecting the infectivity or in vivo transmission capacity of a sample suspected on containing an infectious prion. It is expected that such transgenic animals would produce a phenotype more rapidly than the currently available transgenic animals used for detecting $PrP^{Sc}$.

Furthermore, animals expressing the nucleic acid molecule of the invention can be used for the more detailed characterization of prion-associated diseases to lead to elucidation of the pathogenesis of the progressive neurologic pathology and determination of the sequence of molecular events. The animals are useful for studying various proposed mechanisms of the pathogenesis of these diseases in order to lead to better treatments for the diseases.

Animals expressing the nucleic acid molecule of the invention are also useful for the identification of previously unrecognized genes which also play a role in prion-associated diseases, either beneficial or deleterious. A transgenic animal bearing a candidate gene is crossed with an animal expressing a nucleic acid molecule of the invention and the effect of the presence of the candidate gene on the prion-associated disease-related traits of the transgenic animal are examined.

A candidate gene can be scored as beneficial if it delays or dilutes a prion-associated disease-related phenotype such as loss of motor control, dementia, paralysis wasting and death, typically following pneumonia.

Conversely, a candidate gene can be scored as favoring the development of a prion-associated disease if it advances or enhances a disease-related phenotype.

The invention is described in greater detail by the following non-limiting examples.

EXAMPLE 1

Animal and Reagent Sources

Specific-pathogen-free 3-week old female Golden Syrian hamsters were obtained from Charles River Laboratories (Wilmington, Mass.). Apyrase, DEPC, Cyclic 2',3'-GMP, 3'-CMP, heparinase III, heparan sulfate proteoglycan (MW >200,000), polyadenylic acid (MW 200,000-2,000,000), and polyglutamic acid (MW 50,000-100,000) were obtained from Sigma (St. Louis, Mo.). RNase-free DNase, micrococcal nuclease, RNase A, and DNase-free RNase were obtained from Roche (Indianapolis, Ind.). RNase T1 was obtained from EPICENTRE® (Madison, Wis.). Recombinant benzonase nuclease was purchased from NOVAGEN® (Madison, Wis.). EcoRI was obtained from GIBCO™ BRL (Carlsbad, Calif.). RNase H and RNase V1 were obtained from Ambion (Austin Tex.).

Total brain ganglioside extract and ammonium salt were obtained from Avanti Polar Lipids (Alabaster, AL) and resuspended in 1% TRITON® X-100. Glycogen was obtained from INVITROGEN™ (Carlsbad, Calif.). Sodium pentosan polysulfate was obtained from the TSE Resource Center (Compton, UK) and dissolved in RNase-free 1× TE (10 mM Tris, 1 mM EDTA), pH 8.0 (AMBION®, Austin, Tex.). Heparan sulfate proteoglycan prepared from the basement membrane of Engelbreth-Holm-Swarm mouse sarcoma cells (molecular mass >400 kDa), heparan sulfate, sodium salt from bovine kidney (molecular mass, ~12-14 kDa), and polyglutamate (molecular mass, ~50-100 kDa) were all obtained from Sigma (St. Louis, Mo.).

All synthetic polynucleotides were purchased from Sigma (St. Louis, Mo.). The size distributions of these various commercial preparations were determined by a combination of agarose gel electrophoresis and size exclusion high performance liquid chromatography techniques. The preparations assayed were: poly(A), 0.2-6 kb by agarose gel electrophoresis; poly(C), ~6 kb by size exclusion high performance liquid chromatography; poly(G), ~0.2 kb by agarose gel electrophoresis; poly(U), 0.3-1 kb by size exclusion high performance liquid chromatography; poly(dA), ~1.5-4 kb by agarose gel electrophoresis; poly(dT), ~1.5-4 kb by agarose gel electrophoresis; and poly(dC), 0.39 kb, according to manufacturer). Stock solutions of synthetic polynucleotides were prepared in 1× TE pH 8.0, and concentrations were confirmed by $A_{260}$ nm.

EXAMPLE 2

In Vitro $PrP^{Sc}$ Amplification

In vitro $PrP^{Sc}$ amplification (Lucassen, et al. (2003) supra) and PMCA (Saborio, et al. (2001) supra) were performed as described, except that normal brain homogenates were prepared with EDTA-free Complete Protease inhibitors (Roche, Indianapolis, Ind.) to facilitate experiments involving metal-dependent enzymes. Two millimolar $MgCl_2$ was added to reactions with benzonase and 2 mM $CaCl_2$ was added to reactions with micrococcal nuclease and apyrase. All amplification and control reactions were performed at 37° C. for 16 hours. For PrP$^{Sc}$ detection, protease digestion was performed with 50 µg/ml proteinase K for 1 hour at 37° C. and immunoblotting was performed with 3F4 monoclonal antibody (Signet, Dedham, Mass.).

For experiments testing purified or synthetic compounds, each 100-µl amplification reaction contained 2.5 µg/ml PrP$^C$ and 10 ng/ml PrP27-30 in 0.75× PBS, 0.25× TE, 0.2-0.75% TRITON® X-100, 2 mM EDTA. In experiments testing the effects of Prnp$^{0/0}$ mouse brain homogenate, each sample contained 5 µg/ml PrP$^C$ and 10 ng/ml PrP27-30 in PBS, 0.75% TRITON® X-100, 2 mM EDTA plus 2.5% (w/v) Prnp$^{0/0}$ mouse brain post-nuclear supernatant or buffer. Samples were mixed at 37° C. and shaken overnight at 800 rpm (EPPENDORF® Thermomixer, Fisher Scientific). To detect PrP$^{Sc}$, each sample was incubated with 60 µg/ml proteinase K for 40 minutes at 37° C., boiled in SDS sample buffer, and subjected to western blot analysis using 3F4 monoclonal antibody (Lucassen, et al. (2003) supra).

EXAMPLE 3

RNase A Inactivation

Pure RNase A (50 µg) was incubated with 1% DEPC in 100 µl at room temperature for 2 hours. Following incubation, the reaction was dialyzed twice against 1L 10 mM Tris pH 7.2 at 4° C. using a 3500 MW SLIDE-A-LYZER® Mini dialysis unit (Pierce, Rockford, Ill.) to remove free DEPC. Control samples containing active RNase A were dialyzed in parallel. Protein recovery>90% was confirmed by BCA assay (Pierce, Rockford, Ill.).

EXAMPLE 4

Nuclease Pretreatment of Brain Homogenates for Reconstitution Assays

Nuclease digestion prior to reconstitution was performed by incubating a batch of normal brain homogenate (10% w/v) with benzonase (final concentration of 2.5 units/µl) and 2 mM $CaCl_2$ for 16 hours at 4° C. in the absence of detergents. Benzonase was then inactivated by the addition of 5 mM EDTA prior to reconstitution with RNA or other polyanions.

EXAMPLE 5

Preparation and Measurement of RNA

RNA was isolated from animals less than five minutes after sacrifice using rotor-stator homogenization, extraction with TRIZOL® reagent (INVITROGEN™, Carlsbad, Calif.), and isopropanol precipitation according to manufacturer's instructions, using RNase-free reagents, containers, and equipment. For yeast, cell walls were disrupted during extraction using well-established methods using TRIZOL® in place of phenol (Chapon, et al. (1997) RNA 3:1337-51). All RNA solutions were alcohol-precipitated, washed, and resuspended in RNase-free water prior to use. The concentration and purity of each solution was determined by spectroscopic measurement of optical density at $\lambda_1/\lambda_2$=260/280 nm and confirmed by agarose gel electrophoresis.

EXAMPLE 6

RNA Size Fractionation

Total hamster brain RNA (0.4 mg) was diluted into 0.8 ml RNase-free water, loaded in 0.2 ml batches onto four separate Centrex UF-05 (100,000 MW cutoff) ultrafiltration devices (Schleicher and Schuell, Keene, N.H.), and centrifuged for 15 minutes at 3000×g. The devices were then washed with an equal volume of water. The filtrates were pooled and retentate fractions collected by briefly centrifuging the ultrafiltration devices upside-down into new microcentrifuge tubes. Parallel samples of denatured retentate were prepared in 50% formamide to disrupt all intra- and inter-molecular interactions.

Total RNA was also fractionated using oligo dT column chromatography. Three milligrams of total hamster liver RNA was applied to a single QIAGEN® Mega OLIGOTEX® column according to manufacturer's instructions. RNA isolated from the column included poly(A)$^-$ (flow-through) and poly(A)$^+$ (eluate). PrP$^{Sc}$ amplification of a mixture of 0.05% hamster scrapie brain homogenate and 10% normal hamster brain homogenate was conducted in the presence of poly(A)$^-$, poly (A)$^+$ or total RNA each at a final concentration of 0.5 mg/ml. Amplification was carried out at 37° C. for 16 hours prior to Proteinase K digest.

Size separation of the poly(A)$^-$ RNA was conducted on a 5-35% sucrose gradient using standard methods. Alternatively, synthetic poly(A) (Sigma, St. Louis, Mo.) was resuspended in 1× TE, pH 8.0, and the concentration was confirmed by $A_{260\ nm}$. A sample containing 200 µg of this preparation was electrophoresed on a 1% agarose gel. Unstained slices corresponding to different mobility ranges were excised and extracted using a gel-extraction kit (QIAGEN®, Valencia, Calif.). Poly(A) 45-, 25-, and 10-mer oligonucleotides were purchased from IDT (Coralville, Iowa) and resuspended in 1× TE, pH 8.0. Concentrations of each poly(A) fraction were determined by $A_{260\ nm}$.

EXAMPLE 7

IgG Cross-Linked Protein A-Agarose Beads

All procedures were performed at room temperature. Four hundred microliters of IMMUNOPURE® Immobilized Protein A Plus 50% slurry (Pierce, Rockland, Ill.) was mixed with 16 µg IgG per microliter of packed resin for 2 hours. Following incubation, agarose beads were recovered by centrifugation at 1000×g for 1 minute and washed twice with 1 ml of 200 mM triethanolamine, pH 8.0 (Acros Organics, Geel, Belgium). Antibodies were cross-linked by incubation in 1 ml of 10 mM dimethyl pimelimidate hydrochloride (Pierce, Rockland, Ill.), 200 mM triethanolamine, pH 8.0, for 30 minutes. The reaction was quenched by the addition of 50 µl of 1 M Tris, pH 8.0, and beads were recovered by centrifugation at 1000×g for 1 minute. Cross-linked beads were then washed three times, once in phosphate-buffered saline without calcium or magnesium (PBS), 1% TRITON® X-100, and twice in PBS. Beads were resuspended in 200 µl of PBS and stored at 4° C.

EXAMPLE 8

Immunopurification of PrP$^C$

All procedures were performed at 4° C. Four brains, including cerebellum and brainstem, from 8- to 12-week-old specific-pathogen-free Golden Syrian hamsters of either sex were homogenized in 10 volumes (w/v) of ice-cold PBS plus COMPLETE® protease inhibitors (Roche Applied Science, Indianapolis, Ind.) using a Biohomogenizer Mixer (Biospec Products, Bartlesville, Okla.) at 7,000 rpm for 30-60 seconds. The homogenate was centrifuged at 3,200×g for 20 minutes, and the pellet was resuspended in 40 ml of PBS, 1% sodium deoxycholate (DOC), 1% TRITON® X-100, and COMPLETE® protease inhibitors using a Wheaton glass Dounce homogenizer (10 strokes with pestle B). The sample was incubated on ice for 30 minutes and then centrifuged at 100,000×g for 30 minutes. The solubilized supernatant was removed and placed into a 50-ml conical tube with 400 µl of either D13 or 3F4 cross-linked protein A-agarose beads (50% slurry) and incubated end-over-end for 2 hours. Beads were centrifuged at 1,000×g for 2 minutes, and the supernatant was discarded. The beads were then washed once with 50 ml of IMMUNOPURE® Gentle Ag/Ab Binding Buffer (Pierce, Rockland, Ill.), transferred to a microcentrifuge tube, and washed in 1 ml of the same buffer. The beads were eluted twice with 500 µl of IMMUNOPURE® Gentle Ag/Ab Elution Buffer (Pierce, Rockland, Ill.). The two eluate volumes were combined, diluted with 47 ml of IMAC-$CuSO_4$ wash buffer (20 mM MOPS, pH 7.0, 0.15 M NaCl, 10 mM imidazole, 1% TRITON®) plus EDTA-free COMPLETE® protease inhibitors (Roche Applied Science, Indianapolis, Ind.), incubated with 2 ml of pre-equilibrated IMAC-$CuSO_4$ resin (Amersham Biosciences, Piscataway, N.J.) on an end-over-end rotator for 30 minutes, and centrifuged for 2 minutes at 1,000×g. The supernatant was removed and discarded, and the resin was washed twice in 50 ml of IMAC-$CuSO_4$ wash buffer. $PrP^C$ was then eluted in 6 ml of IMAC-$CuSO_4$ elution buffer (20 mM MOPS, pH 7.5, 0.15 M NaCl, 0.15 M imidazole, 1% TRITONO® X-100) containing EDTA-free COMPLETE® protease inhibitors. Typically, the yield of $PrP^C$ was ~10-fold higher when crosslinked 3F4 beads were used than when cross-linked D13 beads were used.

Desalted purified $PrP^C$ substrate (preparation "X") was immunopurified according to the method above with the exception that the eluate was buffer exchanged into 20 mM MOPS, pH 7.0, 0.15 M NaCl, 0.2% TRITON® X-100 containing COMPLETE® protease inhibitors. Metal-free purified $PrP^C$ substrate (preparation "Y") was immunopurified as above with the exception that the eluate was dialyzed for 16 hours at 4° C. using Pierce SLIDE-A-LYZER® cassette (Molecular weight cutoff 3500) into 2 changes of 20 mM MOPS, pH 7.0, 0.15 M NaCl, 0.2% TRITON® X-100. Imidazole-insensitive purified $PrP^C$ substrate (preparation "Z") was immunopurified as above with the exception that instead of purification via an IMAC-$CuSO_4$ column, the sample was applied to a ZEBA™ desalting spin column (Pierce, Rockland, Ill.) pre-equilibrated in Buffer 20 mM MOPS, pH 7.0, 0.15 M NaCl, 0.2% Triton, and then passed over a 1 ml uncharged chelating SEPHAROSE™ column (Amersham, Piscataway, N.J.).

The following protocol was used to prepare the imidazole-insensitive $PrP^C$ substrate used in analyzing divalent metal compound inhibition of $PrP^C$ conversion. All procedures were performed at 4° C. Six frozen brains from 8-12-week-old golden Syrian hamsters of either sex (Harlan Bioproducts, Indianapolis, Ind.) were homogenized in ~6 volumes (w/v) of ice-cold (PBS) plus COMPLETE® protease inhibitors (Roche, Indianapolis, Ind.) using a Biohomogenizer Mixer (Biospec Products, Bartlesville, Okla.) at 7000 rpm for 30-60 seconds. The homogenate was centrifuged at 3,200×g for 20 minutes, and the pellet was resuspended in 40 ml PBS, 1% DOC, 1% TRITON® X-100 and COMPLETE® protease inhibitors using a Wheaton glass Dounce homogenizer (10 strokes with pestle B). The homogenate was solubilized by incubation on ice for 30 minutes, and then centrifuged at 100,000×g for 30 minutes. The supernatant filtered using 0.2 μm STERICUPS™ (MILLIPORE®, Billerica, Md.) was poured over a 1 ml protein A column to pre-clear tissue-derived immunoglobulins, and the flow-through was collected and passed over a Econ-Pac column (BIO-RAD®, Hercules, Calif.) packed with 1 ml IMMUNOPURE® Immobilized Protein A (Pierce, Rockland, Ill.) cross-linked to 3F4 antibody. The column was washed with 20 ml 20 mM Tris, pH 8.0, 0.5 M NaCl, 5 mM EDTA followed by 15 ml PBS, 0.5% TRITON®. The column was eluted with 6 ml 0.1M glycine, pH 2.5 followed by 1.2 ml PBS, 1% TRITON®, and the eluate was neutralized by addition of 800 μl M Tris pH 9.0. The neutralized eluate was then applied to ZEBA™ desalting spin columns (Pierce, Rockland, Ill.) pre-equilibrated in 20 mM MES pH 6.4, 0.15 M NaCl, 1% TRITON®. The 8 ml buffer-exchanged sample was then passed over a 1.5 ml SP SEPHAROSE™ ion exchange column (Sigma, St. Louis, Mo.), and the column was washed with 15 ml 20 mM MOPS pH 7.0, 0.25 M NaCl, 1% TRITON®. The column was eluted with 8 ml 20 mM MOPS, pH 7.0, 0.5 M NaCl, 1% TRITON® and applied to ZEBA™ desalting spin columns pre-equilibrated with 20 mM MOPS, pH 7.0, 0.15 M NaCl, 0.2% TRITON® to yield the final product.

EXAMPLE 9

Purification of $PrP^C$ by Conventional Affinity Chromatography

An alternative protocol for purifying $PrP^C$ from hamster brain was based on a modification of an established method (Pan, et al. (1993) supra; Pan, et al. (1992) supra). All procedures were performed at 4° C. Ten hamster brains were homogenized in 5 volumes (w/v) of ice-cold PBS with COMPLETE® protease inhibitors using a Potter homogenizer. The homogenate was centrifuged at 100×g for 30 seconds, and the post-nuclear supernatant was removed and centrifuged at 3,200×g for 20 minutes. The resulting pellet was resuspended in 45 ml of 20 mM MOPS, pH 7.0, 0.15 M NaCl, 1% sodium deoxycholate, 1% TRITON® X-100, 10 mM imidazole, containing EDTA-free COMPLETE® protease inhibitors, homogenized with a Dounce homogenizer, and incubated on ice for 30 minutes to allow for membrane solubilization. The solubilized homogenate was centrifuged at 100,000×g for 30 minutes, and the supernatant was applied to a pre-equilibrated 2-ml IMAC-$CuSO_4$ column (Amersham Biosciences, Piscataway, N.J.). The column was washed with 20 ml of IMAC-$CuSO_4$ wash buffer and eluted with 10 ml of IMAC-$CuSO_4$ elution buffer containing EDTA-free COMPLETE® protease inhibitors. The eluate was applied to a pre-equilibrated 2-ml wheat germ agglutinin column (Vector Laboratories, Burlingame, Calif.), washed with 20 ml of 20 mM MOPS, pH 7.5, 0.15 M NaCl, 1% TRITON® X-100, and eluted with 10 ml of 20 mM MOPS, pH 7.5, 0.15 M NaCl, 50 mM N-acetylglucosamine, 1% TRITON® X-100 containing EDTA-free COMPLETE® protease inhibitors.

EXAMPLE 10

Preparation of PrP 27-30

Post-nuclear brain supernatants were prepared from Sc237 scrapie-infected brains using standard methods (Lucassen, et al. (2003) supra). One milliliter of Sc237 post-nuclear brain supernatant (0.4% w/v) in PBS-1% TRITON® X-100 was incubated with 10 μg/ml Proteinase K (PK, specific activity, 30 units/mg, Roche Applied Science, Indianapolis, Ind.) for 30 minutes at 37° C. Protease digestion was terminated by addition of 5 mM phenylmethylsulfonyl fluoride (from a 0.3 M stock solution in methanol). The digested sample was centrifuged for 1 hour at 100,000×g at 4° C., and resuspended in 100 μl of ice-cold PBS-1% TRITON® X-100 by 10×5 second pulses of direct sonication with a Bandelin Sonopuls ultrasonicator delivering ~55% power to the probe tip (Amtrex Technologies, Saint-Laurent, Canada). After addition of 100 μl of ice cold PBS-1% TRITON® X-100, the sample was sonicated for an additional 10 pulses as above. An additional 800 μl of ice-cold PBS-1% TRITON® X-100 was added, and the sample was centrifuged at 100,000×g for 30 minutes at 4° C. The pellet was subjected to another identical round of resuspension and sonication to generate the final 1 ml of sample containing ~10 ng/ml PrP27-30 in PBS plus 1% TRITON® X-100.

EXAMPLE 11

Quantitation of $PrP^C$ and PrP27-30

$PrP^C$ and PrP27-30 were quantified by comparing dilutions of these preparations against known amounts of recombinant $PrP^C$ on western blots (Prionics, Schlieren, Switzerland). Densitometric measurement of membrane marker film signals was performed through the analysis of multiple film exposures to ensure that comparisons were made within the linear range of the film. Signals within the linear range were quantified using the histogram functions in ADOBE® PHOTOSHOP® and calibrated against the background signal. Serial dilutions of normal hamster brain were used to calibrate densitometric measurements.

EXAMPLE 12

$PrP^C$ Protease Resistance Assay

Each 100 μl amplification reaction contained 250 ng/ml $PrP^C$ and 100 μM $CuCl_2$, $MnCl_2$, $ZnCl_2$, or $CoCl_2$. The components were mixed and incubated for 16 hours at 37° C. A fraction of each sample was treated with 30 μg/ml proteinase K for 50 minutes at 37° C., boiled in SDS sample buffer, and subjected to western blot analysis using 3F4 monoclonal antibody.

EXAMPLE 13

Ultracentrifugation $PrP^C/PrP^{Sc}$ Binding Assay

Each reaction volume was 100 μl. Purified $PrP^C$ was added where indicated at a concentration of 250 ng/ml, PrP27-30 was added where indicated at a concentration of 50 ng/ml, and $CuCl_2$ was added where indicated at a concentration of 1 μM. The components were added to each reaction and brought up to 100 μl with 20 mM MOPS, pH 7.0, 0.15 M NaCl, 0.2% TRITON®. The samples were incubated for 16 hours at 4° C. The samples were then diluted to 1 ml with 20 mM MOPS, pH 7.0, 0.15 M NaCl, 0.2% TRITON® and centrifuged for 30 minutes at 100,000×g. The supernatant was removed down to ~100 μl residual volume so as not to disturb the pellet and 900 μl 20 mM MOPS, pH 7.0, 0.15 M NaCl, 0.2% TRITON® was added. The samples were centrifuged again for 30 minutes at 100,000×g, and 900 μl supernatant was again removed. The remaining 100 μl pellets were boiled in SDS sample buffer, and subjected to western blot analysis using 3F4 monoclonal antibody. The intensity of $PrP^C$ and PrP27-30 bands was quantitated on non-saturated film exposures using the histogram function in ADOBE® PHOTOSHOP® software, and the degree of binding was calculated as a ratio of these bands.

What is claimed is:

1. A method for identifying the presence of $PrP^{sc}$ comprising
   (a) contacting a sample suspected of containing an infectious prion protein with
      (i) a substantially purified preparation of $PrP^c$ obtained by immunoaffinity chromatography and ion exchange chromatography, wherein the substantially purified preparation is a preparation that comprises at least 95% $PrP^c$, and
      (ii) a nucleic acid molecule which enhances the amplification of $PrP^{sc}$, wherein said nucleic acid molecule comprises at least 300 bases; and
   (b) identifying the presence of $PrP^{sc}$.

* * * * *

UNITED STATES PATENT AND TRADEMARK OFFICE
CERTIFICATE OF CORRECTION

| | | |
|---|---|---|
| PATENT NO. | : 7,871,776 B2 | Page 1 of 1 |
| APPLICATION NO. | : 12/090101 | |
| DATED | : January 18, 2011 | |
| INVENTOR(S) | : Supattapone et al. | |

It is certified that error appears in the above-identified patent and that said Letters Patent is hereby corrected as shown below:

In the title, please delete "PRIOR".

In the title, please insert -- PRION --.

Signed and Sealed this
Twenty-second Day of March, 2011

David J. Kappos
*Director of the United States Patent and Trademark Office*

UNITED STATES PATENT AND TRADEMARK OFFICE
CERTIFICATE OF CORRECTION

PATENT NO. : 7,871,776 B2  Page 1 of 1
APPLICATION NO. : 12/090101
DATED : January 18, 2011
INVENTOR(S) : Supattapone et al.

It is certified that error appears in the above-identified patent and that said Letters Patent is hereby corrected as shown below:

Title Page, Item (54) and at column 1, line 3,

In the title, please delete "PRIOR" and insert -- PRION --.

This certificate supersedes the Certificate of Correction issued March 22, 2011.

Signed and Sealed this
Twenty-sixth Day of April, 2011

David J. Kappos
*Director of the United States Patent and Trademark Office*